United States Patent [19]

Georgiev et al.

[11] Patent Number: 4,614,810

[45] Date of Patent: Sep. 30, 1986

[54] 4,5-DIHYDRO-4-OXO-2-[(2-TRANS-PHENYL-CYCLOPROPYL)AMINO]-3-FURANCARBOXYLIC ACIDS AND DERIVATIVES THEREOF

[75] Inventors: Vassil S. Georgiev; Robert A. Mack, both of Rochester; Clyde R. Kinsolving, Fairport, all of N.Y.

[73] Assignee: Pennwalt Corporation, Philadelphia, Pa.

[21] Appl. No.: 653,254

[22] Filed: Sep. 24, 1984

[51] Int. Cl.$^4$ ............................................. C07D 307/68
[52] U.S. Cl. ...................................................... 549/479
[58] Field of Search .......................................... 549/479

[56] References Cited

PUBLICATIONS

Lorian, Antibiotics in Laboratory Mediane, Williams & Wilkins, Baltimore, 1980, pp. 506–517.
Capuano et al., Chem. Ber., vol. 109 (1976) pp. 212–217.

*Primary Examiner*—Richard L. Raymond

[57] ABSTRACT

4,5-dihydro-4-oxo-2-[(2-trans-phenylcyclopropyl)amino]-3-furancarboxylic acids and derivatives are described.

11 Claims, No Drawings

4,5-DIHYDRO-4-OXO-2-[(2-TRANS-PHENYLCYCLOPROPYL)AMINO]-3-FURANCARBOXYLIC ACIDS AND DERIVATIVES THEREOF

BACKGROUND OF THE INVENTION

This invention relates generally to 2-[(N-substituted)amino]-4,5-dihydro-4-oxo-3-furancarboxylic acids and more specifically to 4,5-dihydro-4-oxo-2-[(2-trans-phenylcyclopropyl)amino]-3-furancarboxylic acids and derivatives thereof.

A series of 2-[(N-substituted)amino]-4,5-dihydro-4-oxo-3-furancarboxylic acids and their ethyl esters have been described in the literature, for example by Capuano et al in Chem. Ber. 109, pp. 212–217 (1976). We have found that some of these compounds possess anti-inflammatory activity in the carrageenan-induced rat paw edema assay, but no antimicrobial activity. We have now prepared new 2-[(N-substituted)amino]-4,5-dihydro-4-oxo-3-furancarboxylic acid derivatives which contain the (trans-phenylcyclopropyl)amino moiety. The new compounds show antimicrobial activity against a variety of bacteria.

SUMMARY OF THE INVENTION

In accordance with this invention there are provided 4,5-dihydro-4-oxo-2-[(2-trans-phenylcyclopropyl)amino]-3-furancarboxylic acids or derivatives thereof having the general formula:

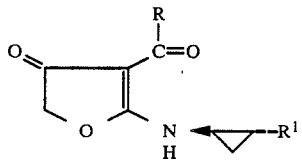

Where R is selected from hydroxy, lower alkoxy, and O-alkali metal; and where $R^1$ is selected from phenyl and substituted phenyl.

DETAILED DESCRIPTION

The compounds of the invention are carboxylic acids and acid derivatives including alkali metal salts of the acid and esters formed from lower alkyl alcohols. Examples of $R^1$ in the general formula include phenyl and substituted phenyl wherein the term "substituted phenyl" as used herein refers to phenyl substituted with lower alkyl and/or halogen (chlorine, fluorine, bromine, iodine), preferably chlorine. The terms "lower alkyl" and "lower alkoxy" as used herein refer to straight and branched chain alkylene groups having 1 to 8 carbon atoms.

The compounds of the invention can be prepared as illustrated in the following diagram which involves a base-catalyzed cyclocondensation of ethyl-4-chloroacetoacetate I with an appropriate trans-phenylcyclopropyl isocyanate II to provide the esters III. Alkaline hydrolysis of esters III gives the corresponding free acids IV. In addition, treatment of the free acids IV with sodium carbonate (or another alkali metal carbonate) gives the salts VII.

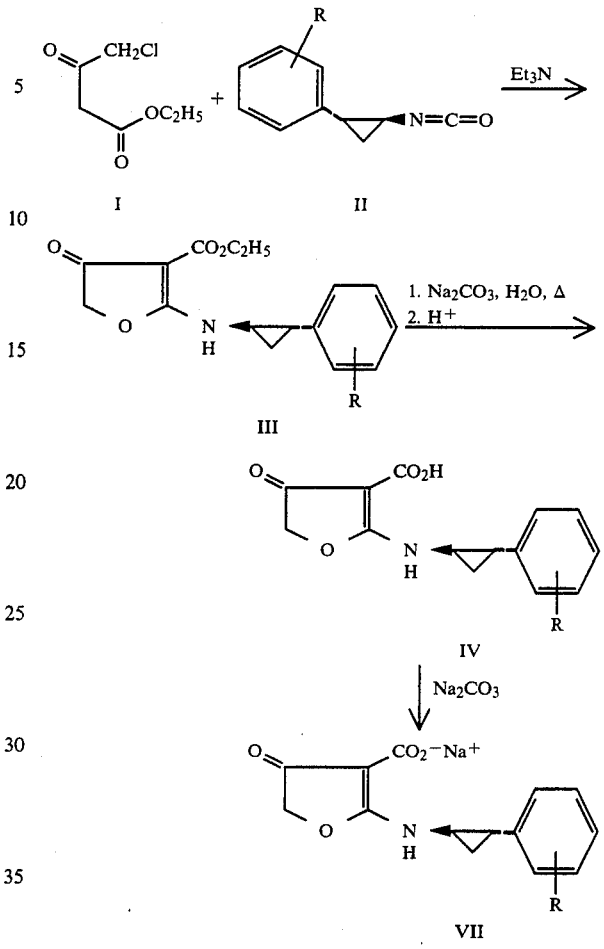

Non-limiting examples of specific compounds according to the invention and their preparation are illustrated in the following examples.

EXAMPLE 1

4,5-Dihydro-4-oxo-2-[2-(trans-phenylcyclopropyl)amino]-3-furancarboxylic Acid Ethyl Ester (1)

Under nitrogen atmosphere, triethylamine (4.5 ml) was added dropwise over 15 min. to a well-stirred solution of trans-phenylcyclopropyl isocyanate (5.45 grams) and ethyl 4-chloroacetoacetate (4.50 grams) in petroleum ether-ethyl acetate (10:1 by volume), at 5°–10° C. (ice/water bath). During the addition, a heavy precipitate formed. The reaction mixture was stirred at 0°–5° C. for 1 hour, and the precipitate was filtered off under vacuum. The solid was stirred for 1 hour in petroleum ether, filtered and stirred with 1N hydrochloric acid. The filter cake was rinsed with water, then sucked dry on the filter. Recrystallization from isopropanol gave 5.54 grams of compound 1 as a white crystalline product melting at 140°–142° C. This compound showed antimicrobial activity against several bacteria in broth and agar dilution tests.

EXAMPLE 2

4,5-Dihydro-4-oxo-2-[[2-trans-(4-chlorophenyl)cyclopropyl]amino]-3-furancarboxylic Acid Ethyl Ester (2)

Compound 2 was prepared by a similar process to that described in Example 1 with trans-4-chlorophenylcyclopropyl isocyanate being reacted with ethyl 4-chloroacetoacetate.

EXAMPLE 3

4,5-Dihydro-4-oxo-2-[[2-trans-(4-methylphenyl)cyclopropyl]amino]-3-furancarboxylic Acid Ethyl Ester (3)

Compound 3 was prepared by a similar process to that described in Example 1 with trans-4-(methylphenyl)cyclopropyl isocyanate being reacted with ethyl 4-chloroacetoacetate.

EXAMPLE 4

4,5-Dihydro-4-oxo-2-[(2-trans-phenylcyclopropyl)amino]-3-furancarboxylic Acid (4)

4,5-Dihydro-4-oxo-2-[(2-trans-phenylcyclopropyl)amino]-3-furancarboxylic acid ethyl ester (1) (15.50 grams, 54 mmol) was added to a solution of sodium carbonate (11.45 grams, 108 mmol) in 170 ml water. Steam was then passed through the mixture for 2 hours. After refluxing for 1 additional hour, the reaction mixture was cooled to 5°–10° C. and filtered in order to remove some solid impurities. Acidification to pH 1 with concentrated hydrochloric acid precipitated the free acid. The latter was recrystallized from ethanol to give 7.15 grams of compound 4 melting at 155°–157° C. This compound showed antimicrobial activity against a variety of bacteria in broth and agar dilution tests.

EXAMPLES 5 and 6

4,5-Dihydro-4-oxo-2-[[2-trans-(4-methylphenyl)cyclopropyl]amino]-3-furancarboxylic Acid (5); and
4,5-Dihydro-4-oxo-2-[[2-trans-(4-chlorophenyl)cyclopropyl]amino]-3-furancarboxylic Acid (6)

Compounds 5 and 6 were prepared by treatment of esters 3 and 2 respectively with sodium carbonate followed by precipitation with concentrated hydrochloric acid similar to the process of Example 4.

EXAMPLE 7

4,5-Dihydro-4-oxo-2-[(2-trans-phenylcyclopropyl)amino]-3-furancarboxylic Acid Sodium Salt (7)

The compound 4, (5.05 grams, 19.5 mmol), was neutralized with sodium carbonate (2.56 grams, 24.2 mmol) in 150 ml water. The solution was warmed to 50° C., then filtered and concentrated to 50 ml under vacuum. The addition of a small amount of ethanol caused a rapid crystallization of the sodium salt 7. Recrystallization from water provided 4.66 grams of pure sodium salt as the monohydrate.

TABLE I
Substituted 4,5-Dihydro-4-oxo-2-[2-trans-phenylcyclopropyl)amino]-3-furancarboxylic Acids and Derivatives

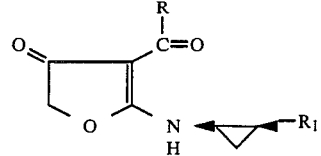

| Compound No. | R | $R^1$ | mp,°C. | recrystn solvent | formula |
|---|---|---|---|---|---|
| 1. | $OC_2H_5$ | $C_6H_5$ | 140–142 | isopropanol | $C_{16}H_{17}NO_4$ |
| 2. | $OC_2H_5$ | $C_6H_4Cl$—4 | 146–148 | isopropanol | $C_{16}H_{16}ClNO_4$ |
| 3. | $OC_2H_5$ | $C_6H_4CH_3$—4 | 157–165 | isopropanol | $C_{17}H_{19}NO_4$ |
| 4. | OH | $C_6H_5$ | 155–157 | ethanol | $C_{14}H_{13}NO_4$ |
| 5. | OH | $C_6H_4CH_3$—4 | 155–157 | ethanol | $C_{15}H_{15}NO_4$ |
| 6. | OH | $C_6H_4Cl$—4 | 173–175 | ethanol | $C_{14}H_{12}ClNO_4$ |
| 7. | $O^{\ominus}Na^{\oplus}$ | $C_6H_5$ | protracted | — | $C_{14}H_{14}NNaO_5$ |

The foregoing has described novel 4,5-dihydro-4-oxo-2-[(2-trans-phenylcyclopropyl)amino]-3-furancarboxylic acids and derivatives thereof which are useful as antimicrobial materials.

We claim:

1. A 4,5-dihydro-4-oxo-2-[(2-trans-phenylcyclopropyl)amino]-3-furancarboxylic acid or derivative thereof having the general formula:

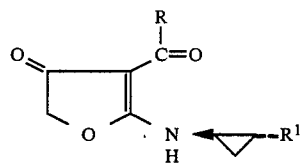

wherein R is selected from hydroxy, lower alkoxy, and O-alkali metal; and where $R^1$ is selected from phenyl and phenyl substituted with lower alkyl and/or halogen.

2. The compound of claim 1 wherein R is hydroxy.

3. The compound of claim 1 wherein R is lower alkoxy.

4. The compound of claim 1 wherein R is O-alkali metal.

5. The compound of claim 1 wherein the compound is 4,5-dihydro-4-oxo-2-[(2-trans-phenylcyclopropyl)amino]-3-furancarboxylic acid ethyl ester.

6. The compound of claim 1 wherein the compound is 4,5-dihydro-4-oxo-2-[[2-trans-(4-chlorophenyl)cyclopropyl]amino]-3-furancarboxylic acid ethyl ester.

7. The compound of claim 1 wherein the compound is 4,5-dihydro-4-oxo-2-[[2-trans-(4-methylphenyl)cyclopropyl]amino]-3-furancarboxylic acid ethyl ester.

8. The compound of claim 1 wherein the compound is 4,5-dihydro-4-oxo-2-[(2-trans-phenylcyclopropyl)amino]-3-furancarboxylic acid.

9. The compound of claim 1 wherein the compound is 4,5-dihydro-4-oxo-2-[[2-trans-(4-methylphenyl)cyclopropyl]amino]-3-furancarboxylic acid.

10. The compound of claim 1 wherein the compound is 4,5-dihydro-4-oxo-2-[[2-trans-(4-chlorophenyl)cyclopropyl]amino]-3-furancarboxylic acid.

11. The compound of claim 1 wherein the compound is 4,5-dihydro-4-oxo-2-[(2-trans-phenylcyclopropyl)amino]-3-furancarboxylic acid sodium salt.

* * * * *